United States Patent
Richter et al.

(10) Patent No.: US 7,067,654 B2
(45) Date of Patent: Jun. 27, 2006

(54) PREPARATION OF POLYISOCYANATES CONTAINING URETDIONE GROUPS

(75) Inventors: Frank Richter, Leverkusen (DE);
Reinhard Halpaap, Odenthal (DE);
Hans-Josef Laas, Bergisch Gladbach (DE); Andreas Hecking, Langenfeld (DE)

(73) Assignee: Bayer MaterialScience AG, Leverkusen (DE)

( * ) Notice: Subject to any disclaimer, the term of this patent is extended or adjusted under 35 U.S.C. 154(b) by 136 days.

(21) Appl. No.: 10/719,175

(22) Filed: Nov. 21, 2003

(65) Prior Publication Data

US 2004/0106789 A1    Jun. 3, 2004

(30) Foreign Application Priority Data

Nov. 25, 2002  (DE)  ............................. 102 54 878

(51) Int. Cl.
*C07D 229/00* (2006.01)
(52) U.S. Cl. ...................................... 540/202
(58) Field of Classification Search .................. 564/1, 564/32, 38; 540/202
See application file for complete search history.

(56) References Cited

U.S. PATENT DOCUMENTS

| | | | | |
|---|---|---|---|---|
| 3,394,111 A | * | 7/1968 | Liebsch | 528/51 |
| 3,645,979 A | | 2/1972 | Liebsch et al. | 260/77.5 NC |
| 3,993,641 A | * | 11/1976 | Tiemann et al. | 540/202 |
| 4,476,054 A | | 10/1984 | Disteldorf et al. | 260/239 |
| 4,614,785 A | | 9/1986 | Richter et al. | 528/45 |
| 4,668,780 A | * | 5/1987 | Disteldorf et al. | 540/202 |
| 4,912,210 A | | 3/1990 | Disteldorf et al. | 540/202 |
| 4,929,724 A | | 5/1990 | Engbert et al. | 540/202 |
| 5,066,436 A | | 11/1991 | Komen et al. | 264/4.3 |
| 5,143,994 A | * | 9/1992 | Laas et al. | 528/45 |
| 5,315,004 A | * | 5/1994 | Goldstein et al. | 540/202 |
| 5,750,629 A | * | 5/1998 | Laas et al. | 528/45 |

FOREIGN PATENT DOCUMENTS

| | | | |
|---|---|---|---|
| DE | 1 934 763 | | 1/1971 |
| GB | 1153815 | | 5/1969 |
| GB | 1 244 416 | * | 9/1971 |

* cited by examiner

*Primary Examiner*—Johann Richter
*Assistant Examiner*—Chukwuma Nwaonicha
(74) *Attorney, Agent, or Firm*—Joseph C. Gil

(57) ABSTRACT

The invention relates to the use of cycloalkylphosphines as catalysts for isocyanate dimerization and to a process for preparing polyisocyanates containing uretdione groups.

13 Claims, 1 Drawing Sheet

PREPARATION OF POLYISOCYANATES CONTAINING URETDIONE GROUPS

CROSS REFERENCE TO RELATED PATENT APPLICATION

The present patent application claims the right of priority under 35 U.S.C. §119 (a)–(d) of German Patent Application No. 102 54 878.1, filed Nov. 25, 2002.

Field of the Invention

The invention relates to the use of cycloalkylphosphines as catalysts for isocyanate dimerization and to a process for preparing polyisocyanates containing uretdione groups.

BACKGROUND OF THE INVENTION

There has not been a lack of attempts to prepare aliphatic polyisocyanates containing uretdione groups and being free as far as possible from by-products, using catalysts whose selectivity is dependent only little, if at all, on temperature and conversion.

Aliphatic isocyanates which contain uretdione groups, have a low by-product content and are based on optionally branched, linear aliphatic diisocyanates are distinguished by a particularly low viscosity; products based on cycloaliphatic diisocyanates can be used as internally blocked crosslinkers, free from elimination products, in coating systems.

Tris(dialkylamino)phosphines (DE-A 3 030 513) optionally in conjunction with cocatalysts (DE-A 3 437 635) exhibit good selectivity for the formation of uretdione groups (uretdione selectivity). Their technical usefulness is hindered, however, by the serious imperfection represented by the high carcinogenic potential of their phosphorus(V) oxide, e.g. hexamethylphosphoric triamide. DE-A 3 739 549 discloses catalytic NCO dimerization with 4-dialkylaminopyridines, such as 4-dimethylaminopyridine (DMAP), for example, but the formation of uretdione is selective only in the case of specific cycloaliphatic isocyanates such as isophorone diisocyanate (IPDI). Linear aliphatic isocyanates such as hexamethylene diisocyanate (HDI) and also branched, linear aliphatic isocyanates such as trimethylhexane diisocyanate (TMDI) and methylpentane diisocyanate (MPDI), when used with DMAP and related compounds, give heterogeneous reaction products which are predominantly highly coloured.

DE-A 1 670 720 discloses the preparation of aliphatic polyisocyanates containing uretdione groups, in which the catalysts used are tertiary phosphines having at least one aliphatic substituent or boron trifluoride and its adducts, respectively. It is noted that high fractions of uretdione groups in the product can be obtained only at low conversions and at reaction temperatures between 50 and 80° C., with the simultaneous formation of isocyanate trimers (isocyanurates and iminooxadiazine-diones) and also, particularly at a relatively high temperature, of other by-products such as carbodiimides or uretonimines. Uretonimines are especially disruptive since they tend to give off monomeric isocyanate during storage.

In order to terminate the reaction at low conversions the phosphine catalysts are deactivated by alkylation with dimethyl sulfate (DE-A 1 670 720) or methyl toluenesulfonate (EP-A 377 177) and then unreacted monomer is removed from the product. This deactivation reaction requires temperatures of up to 60° C. and, on account of its duration, leads to a delay in the actual termination of the reaction of uretdione formation and hence, overall, to the increased formation of by-products.

According to the teaching of DE-A 19 54 093 this problem is circumvented by using elemental sulphur as terminating agent. The reaction is stopped suddenly, independently of the reaction temperature. However, the amount of sulphur required is difficult to determine, since partial catalyst deactivation occurs during the catalysed reaction. Amounts of the catalyst poison used in excess then lead to unadvantageous properties of the polyisocyanate product, such as turbidity, for example, and to problems affecting the reuse of unreacted monomer, as a result of contamination with sulphur.

It was an object of the invention, therefore, to provide a process for preparing isocyanates containing uretdione groups which as compared with the prior art exhibits a greater selectivity for uretdione formation (uretdione selectivity) in conjunction with equal or higher monomer conversions, and where at the same time there should be a distinct reduction in the propensity for uretonimines to form.

SUMMARY OF THE INVENTION

The present invention is directed to a process for preparing polyisocyanates containing uretdione groups. The process includes reacting at least one organic isocyanate, a catalyst comprising at least one phosphine containing at least one cycloaliphatic radical attached directly to phosphorus, optionally one or more solvents, and optionally one or more additives.

DETAILED DESCRIPTION OF THE INVENTION

Figure 1:
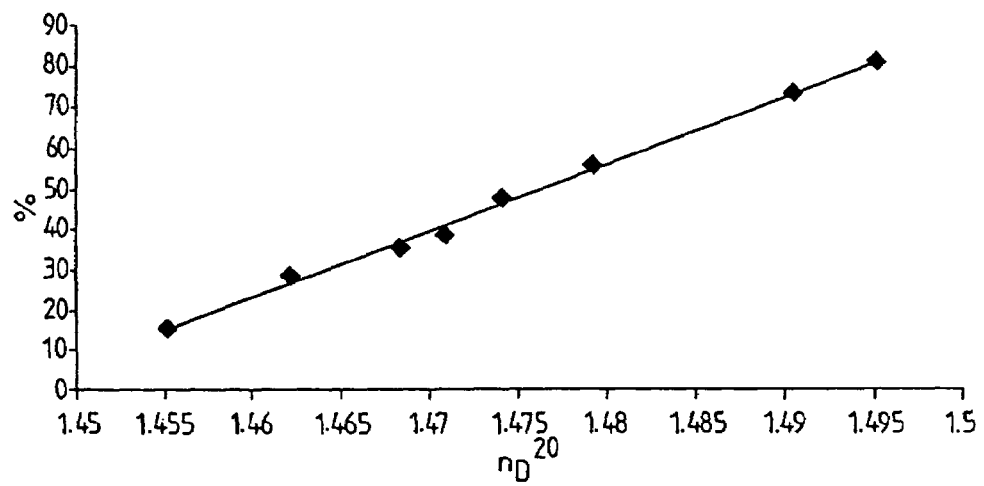
FIG. 1 shows a graph of conversion as a function of refractive index.

It has now been found that cycloalkylphosphines having at least one cycloaliphatic radical attached directly to the phosphorus react more selectively in respect of uretdione formation ("uretdionization") starting from organic isocyanates, and over a broader temperature range, than phosphines with linear aliphatic substitution that have hitherto been used for this purpose. Furthermore, when using the catalysts for use in accordance with the invention, a particularly low propensity for uretonimine to form was found, with a particularly positive consequence for the storage properties of the polyisocyanates prepared.

The invention provides for the use of phosphines having at least one cycloaliphatic radical attached directly to phosphorus as catalysts for uretdione formation (isocyanate dimerization, "uretdionization").

Phosphines for use in accordance with the invention are phosphines of the formula I:

formula I where $R^1$ is an optionally singly or multiply $C_1$–$C_{12}$ alkyl- or alkoxy-substituted cycloaliphatic $C_3$–$C_{20}$ radical and $R^2$, $R^3$ independently of one another is an optionally singly or multiply $C_1$–$C_{12}$ alkyl- or alkoxy-substituted cycloaliphatic $C_3$–$C_{20}$ radical or a linear or branched aliphatic $C_1$–$C_{20}$ radical.

With preference $R^1$ is an optionally singly or multiply $C_1$–$C_{12}$ alkyl-substituted cyclopropyl, cyclobutyl, cyclopentyl or cyclohexyl radical, $R^2$, $R^3$ independently of one another are an optionally singly or multiply $C_1$–$C_{12}$ alkyl-substituted cyclopropyl, cyclobutyl, cyclopentyl or cyclohexyl radical or an aliphatic $C_2$–$C_8$ alkyl radical.

Examples of cycloalkylphosphines for use in accordance with the invention are: cyclopentyldimethylphosphine, cyclopentyl-diethylphosphine, cyclopentyl-di-n-propylphosphine, cyclopentyl-di-isopropylphosphine, cyclopentyl-dibutyl-phosphine, where 'butyl' can stand for all isomers, i.e. n-butyl, iso-butyl, 2-butyl, tert-butyl and cyclobutyl, cyclopentyl-dihexylphosphine (all isomeric hexyl radicals), cyclopentyl-dioctylphosphine (all isomeric octyl radicals), dicyclopentyl-methylphosphine, dicyclopentyl-ethylphosphine, dicyclopentyl-n-propylphosphine, dicyclopentyl-isopropylphosphine, dicyclopentyl-butyl-phosphine (all isomeric butyl radicals), dicyclopentyl-hexylphosphine (all isomeric hexyl radicals), dicyclopentyl-octylphosphine (all isomeric octyl radicals), tricyclopentylphosphine, cyclohexyl-dimethylphosphine, cyclohexyl-di-ethylphosphine, cyclohexyl-di-n-propylphosphine, cyclohexyl-di-isopropylphosphine, cyclohexyl-dibutylphosphine (all isomeric butyl radicals), cyclohexyl-dihexylphosphine (all isomeric hexyl radicals), cyclohexyl-dioctylphosphine (all isomeric octyl radicals), dicyclohexyl-methylphosphine, dicyclohexyl-ethylphosphine, dicyclohexyl-n-propylphosphine, dicyclohexyl-isopropy-lphosphine, dicyclohexyl-butylphosphine (all isomeric butyl radicals), dicyclohexyl-hexylphosphine (all isomeric hexyl radicals), dicyclohexyl-octylphosphine (all isomeric octyl radicals), and tricyclohexylphosphine.

As catalysts for uretdione formation they can be used individually, in any desired mixtures with one another or in mixtures with other primary, secondary and/or tertiary alkyl-, aralkyl- and/or arylphosphines.

The invention further provides a process for preparing polyisocyanates containing uretdione groups, wherein a) at least one organic isocyanate, b) a catalyst comprising at least one phosphine which has at least one cycloaliphatic radical attached directly to phosphorus, c) optionally solvents and d) optionally additives are reacted.

The amount of the catalyst to be used in the process of the invention is guided primarily by the target reaction rate and is situated in the range from 0.01 to 3 mol %, based on the sum of the amounts of substance in mol of the isocyanate used and of the catalyst. It is preferred to use from 0.05 to 2 mol % of catalyst.

In the process of the invention the catalyst b) can be used undiluted or in solution in solvents. Suitable solvents here include all compounds which do not react with phosphines, such as aliphatic or aromatic hydrocarbons, alcohols, ketones, esters, and ethers, for example. Preferably the phosphines are used undiluted in the process of the invention.

As isocyanates for use in accordance with the invention in a) it is possible in principle to use all known organic isocyanates, prepared by phosgenation or by phosgene-free processes, individually or in any desired mixtures with one another.

Preference is given to the use of aliphatic, cycloaliphatic or araliphatic di- or polyisocyanates with an NCO functionality $\geq 2$.

Particular preference is given to the use of optionally branched, aliphatic diisocyanates optionally containing cyclic radicals and having isocyanate groups attached to one primary carbon atom. Examples thereof are butane diisocyanate, pentane diisocyanate, hexane diisocyanate, heptane diisocyanate, octane diisocyanate, nonane diisocyanate, decane diisocyanate, undecane diisocyanate and dodecane diisocyanate, it being possible to employ any isomers of the abovementioned compounds.

In particular use is made of hexamethylene diisocyanate (HDI), methylpentane diisocyanate (MPDI), trimethylhexane diisocyanate (TMDI), bis(isocyanato-methyl)cyclohexane ($H_6$XDI) and norbornane diisocyaate (NBDI) individually or in any desired mixtures with one another.

Furthermore it is possible to use isophorone diisocyanate (IPDI), bis(isocyanato-cyclohexyl)methane ($H_{12}$MDI), bis(isocyantomethyl)benzene (xylylene diisocyanate, XDI) and bis(2-isocyantoprop-2-yl)benzene (tetramethylxylylene diisocyanate, TMXDI) in the process of the invention.

The process of the invention is conducted in the temperature range from 0° C. to 120° C., preferably 0° C. to 100° C., more preferably 0° C. to 80° C., most preferably 0° C. to 60° C.

The process of the invention is carried out so that the conversion of the NCO groups is from 1 to 100 mol %, preferably from 5 to 90 mol %, more preferably from 10 to 60 mol %, most preferably from 10 to 50 mol %.

In order to achieve NCO group conversions <100 mol % the reaction is terminated at the desired degree of conversion.

Catalyst poisons suitable for terminating the reaction after the desired degree of conversion has been achieved include in principle all of those hitherto described (DE-A 1670667, 1670720, 1934763, 1954093, 3437635, U.S. Pat. No. 4,614,785) such as alkylating agents (e.g. dimethyl sulphate, methyl toluenesulphonate), organic or inorganic peroxides, acid chlorides and also sulphur, which are reacted with the catalyst, where appropriate, with an increased temperature (version A).

After the reaction mixture has been deactivated in accordance with version A it is possible for unreacted monomer and/or the deactivated catalyst to be separated off.

The process can also be terminated without chemically deactivating the catalyst. For that purpose, immediately after the desired conversion has been reached, the active catalyst is separated off from the reaction mixture, in order to prevent further reaction with the formation, possibly, of by-product. (Version B).

At the same time as, or else after, the catalyst is separated off it is possible for unreacted residual monomer to be separated off from the reaction mixture treated in accordance with version B.

In the process of the invention unreacted monomers, the catalyst and/or other unwanted constituents can be separated off from the reaction mixture using any known separation techniques such as distillation, extraction or crystallization/filtration, for example. Preference is given to distillation, where appropriate in the specific embodiment of thin-film distillation. It is of course also possible to employ combinations of two or more of these techniques.

For terminating the reaction in accordance with version B it is preferred to remove the catalyst by distillation, in which case it is possible, where appropriate, to remove unreacted monomer at the same time.

In the course of the workup of a reaction terminated in accordance with version A or B the residual monomer present is preferably removed by distillation.

Where the polyisocyanate prepared in accordance with the invention is intended still to contain free, unreacted monomer, such as is of interest, for example, for its further processing to NCO-blocked products or low-NCO or NCO-free polyuretdione curing agents, for example for the powder coating sector, it is possible to forego the separation of monomer after the termination of reaction (versions A and B).

For the conduct of the process of the invention it is irrelevant whether the process is conducted in whole or in part batchwise or continuously.

Furthermore it is possible in the process of the invention to add stabilizers and additives which are customary in polyisocyanate chemistry at any desired point in time. Examples are antioxidants, such as sterically hindered phenols (2,6-di-tert-butylphenol, 4-methyl-2,6-di-tert-butylphenol), for example, light stabilizers, such as HALS amines, triazoles etc., weak acids or catalysts for the NCO—OH reaction, such as dibutyltin dilaurate (DBTL), for example.

Moreover it may be sensible to add small amounts of a catalyst poison for use in version A to a product worked up in accordance with version B, in order to increase the reverse cleavage stability and to reduce the propensity for by-products to be formed and/or for the free NCO groups to react further, in the course of product storage, for example.

Products prepared by the process of the invention and based on optionally branched, linear aliphatic di- or polyisocyanates, containing no cycloalkyl substituents are light in colour and have a viscosity <1000 mPas/23° C. If cycloaliphatic and/or araliphatic di- or polyisocyanates are used the resins obtained range from highly viscous to solid (viscosity >10 000 mPas/23° C.).

In low-monomer form, i.e. after the removal of unreacted monomer, the products of the invention have an NCO content <30% by weight, preferably <25% by weight.

The polyisocyanates prepared by the process of the invention serve as starting materials for producing, for example, mouldings (where appropriate, foamed), paints, coating materials, adhesives or adjuvants, it being possible where appropriate for the free, non-uretdionized NCO groups present to have been blocked.

Methods suitable for blocking the free, non-uretdionized NCO groups include all those known to the skilled worker. As blocking agents it is possible in particular to use phenols (e.g. phenol, nonylphenol, cresol), oximes (e.g. butanone oxime, cyclohexanone oxime), lactams (e.g. ε-caprolactam), secondary amines (e.g. diiso-propylamine), pyrazoles (e.g. dimethylpyrazole), imidazoles, triazoles) or malonic and acetic esters.

The substantially by-product-free polyisocyanates containing uretdione groups that are prepared by the process of the invention can be used in particular for preparing one- and two-component polyurethane coating materials, in mixtures where appropriate with other, prior art di- or polyisocyanates, such as di- or polyisocyanates containing biuret, urethane, allophanate, isocyanurate, and iminooxadiazinedione groups.

Likewise particularly preferred is the use of the polyisocyanates prepared in accordance with the invention on the basis of optionally branched, linear aliphatic isocyanates as reactive diluents for reducing the viscosity of polyisocyanate resins of relatively high viscosity.

For the reaction of the polyisocyanates prepared in accordance with the invention to polyurethane it is possible to use any compounds having at least two isocyanate-reactive functionalities, individually or in any mixtures with one another (isocyanate-reactive binder).

Preference is given to the use of one or more isocyanate-reactive binders which are known per se in polyurethane chemistry, such as polyhydroxy compounds or polyamines. As polyhydroxy compounds it is particularly preferred to use polyester-, polyether-, polyacrylate- and/or polycarboxylic acid-polyols, where appropriate with the addition of low molecular mass polyhydric alcohols as well.

The equivalents ratio between non-uretdionized isocyanate group, which where appropriate may also have been blocked, and isocyanate-reactive functionality of the isocyanate-reactive bonder, such as OH—, NH— or COOH, is from 0.8 to 3, and in some cases from 0.8 to 2.

A possibility is the use of an excess of isocyanate-reactive binder, since the cleavage of the uretdione ring, where appropriate at elevated temperature and/or with addition of catalyst, leads to the liberation of further NCO groups, which are able to react with the excess of isocyanate-reactive functionalities. As a result, the network density of the polymer formed is increased and its properties are advantageously influenced.

For accelerating the crosslinking reaction of polyisocyanates prepared in accordance with the invention with the isocyanate-reactive binder it is possible to use any of the catalysts known from polyurethane chemistry. By way of example it is possible to use metal salts such as dibutyltin (IV) dilaurate, tin(II) bis(2-ethyl-hexanoate), bismuth(III) tris(2-ethylhexanoate), zinc(II) bis(2-ethylhexanoate) or zinc chloride and also tertiary amines such as 1,4-diazabicyclo[2.2.2]octane, triethylamine or benzyldimethylamine.

At the formulation stage the optionally blocked polyisocyanate prepared in accordance with the invention, the isocyanate-reactive binder, catalyst(s) and, where appropriate, the usual extras such as pigments, fillers, additives, levelling assistants, defoamers and/or matting agents are mixed with one another and homogenized in a customary mixing unit such as, for example, a sand mill, where appropriate with the use of solvents.

Suitable solvents include all customary paint solvents known per se, such as ethyl and butyl acetate, ethylene or propylene glycol monomethyl, monoethyl or monopropyl ether acetate, 2-butanone, 4-methyl-2-pentanone, cyclohexanone, toluene, xylene, solvent naphtha, N-methylpyrrolidone, etc.

The coating materials can be applied in solution or from the melt and also, where appropriate, in solid form (powder coating materials) by the customary methods such as spreading, rolling, pouring, spraying, dipping, by the fluid-bed sintering process or by electrostatic spraying processes, for example, to the article that is to be coated.

Suitable substrates include all known materials of construction, especially metals, wood, plastics and ceramic.

EXAMPLES

All percentages are to be understood as being by weight (percent by weight) unless stated otherwise.

The determination of the NCO content of the resins described in the inventive and comparative examples was made by titration in accordance with DIN 53 185.

The dynamic viscosities were determined at 23° C. using a rotational viscometer (ViscoTester® 550, Thermo Haake GmbH, D-76227 Karlsruhe). Measurements were made at different shear rates in order to ensure that the rheology of the described polyisocyanates prepared in accordance with the invention, and that of the comparison products as well, corresponds to that of ideal Newtonian fluids. Accordingly, it is unnecessary to state the shear rate.

The indication 'mol %' or of the molar ratio of different types of structure to one another is based on measurements by NMR spectroscopy. It refers in each case, unless otherwise specified, to the sum of the types of structure formed by the modification reaction (oligomerization) from the previously free NCO groups of the isocyanate to be modified. The $^{13}$C-NMR measurements were made on approximately 50% strength by weight samples in dry $CDCl_3$ or approximately 80% strength by weight samples in $D_6$-DMSO at a proton frequency of 400 or 700 MHz ($^{13}$C-NMR: 100 or 176 MHz, relaxation delay: 4 sec, 2000 scans; spectrometer: DPX 400, AVC 400 or DRX 700, Bruker GmbH, D-76287 Rheinstetten). As a reference for the ppm scale, small amounts of tetramethylsilane were chosen in the solvent, with a $^{13}$C-chem. shift of 0 ppm, or the solvent itself, with a shift of 77.0 ppm ($CDCl_3$) or 43.5 ppm ($D_6$-DMSO).

Unless specified otherwise, the reactions were carried out with HDI as reactant.

Example 1

10 g portions of freshly distilled, degassed HDI were stirred (magnetic stirrer) in glass vessels sealed with septa under nitrogen in the presence of the catalyst amounts indicated in Table 1 and at the stated temperatures, the progress of the reaction being determined at regular intervals by measurement of the refractive index (at 20° C. and the frequency of the light of the D line of the sodium spectrum, $n_D^{20}$) of the reaction mixture (crude material) (start=no conversion=$n^{D20}$ of the pure HDI=1.4523).

TABLE 1

Reaction parameters

| Temperature [° C.] | TBP [mol %]* | CHDHP [mol %]* | DCPBP [mol %]* | TCPP [mol %]* |
|---|---|---|---|---|
| 40 | 0.18 | 0.60 | 0.70 | 1.14 |
| 60 | 0.18 | 0.80 | 0.73 | 1.13 |
| 80 | 0.25 | 0.50 | 0.46 | 1.06 |
| 100 | 0.30 | 0.48 | 0.47 | 1.06 |
| 120 | 0.31 | 0.56 | 0.55 | 1.04 |

*based on amount of HDI used
Abbreviations:
TBP: tri-n-butylphosphine (=> comparative experiments)
CHDHP: cyclohexyl-di-n-hexylphosphine (=> inventive experiment)
DCPBP: dicyclopentyl-butylphosphine (=> inventive experiment)
TCPP: tricyclopentylphosphine (=> inventive experiment)

By recording calibration curves on the basis of relatively large batches worked up by distillation at different degrees of conversion, the $n_D^{20}$ value of the crude substance was related to the resin yield [%], or yield for short hereinbelow, for various catalysts. In the region up to about 80% yield, an approximately linear relationship between the two variables was obtained (FIG. 1) independent of catalyst and reaction temperature, so that the resin yield can always be determined in situ by measuring the refractive index.

Figure 2:
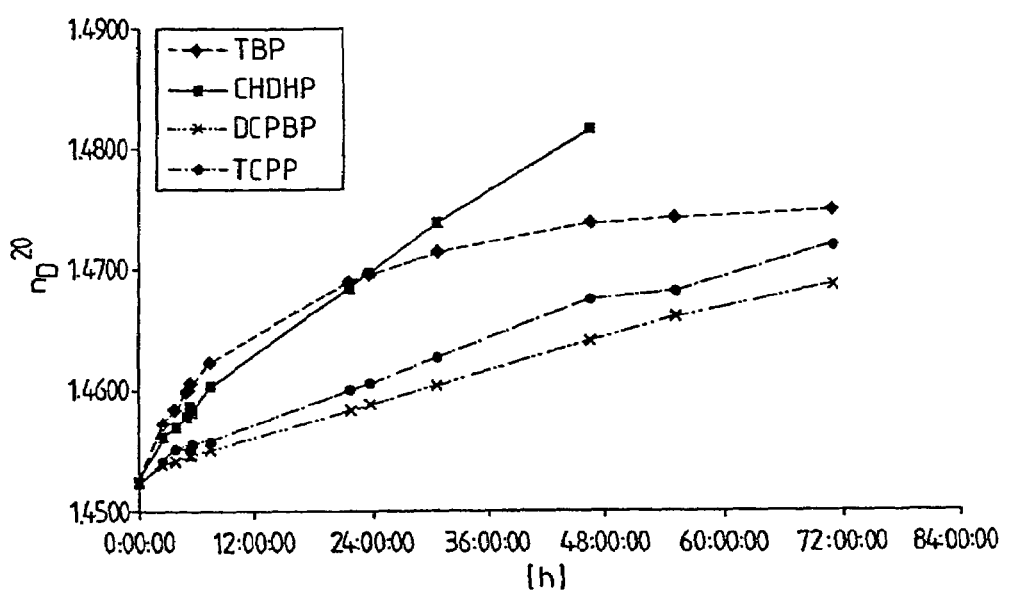
FIG. 2 shows a graph of refractive index as a function of time.

At the same (molar) concentration, tri-n-butylphosphine (TBP) produces a higher reaction rate in comparison with the catalysts for use in accordance with the invention. The latter are less active as the number of P-bonded cycloalkyl groups increases, but at the same time become much more selective in terms of uretdione formation. Consequently the amounts of TBP used are always lower than those of the cycloalkylphosphines, in order to keep the reaction rates comparable. A further factor is that, when TBP is used, a relatively rapid reaction at the start is quickly followed by the onset of catalyst deactivation, evident from the increasingly shallower slope of the time/yield plot as the reaction progresses. With the cycloalkyl-substituted phosphines, in contrast, a substantially more uniform reaction regime is obtained, though still with high yields (FIG. 2). In Example 1 the amount of the catalyst used in each case was guided solely by the target reaction rate. Within the abovementioned limits the concentration of catalyst has no detectable effect on the selectivity of the reaction, as demonstrated on the basis of comparative experiments with a higher TBP concentration at different temperatures.

In order to examine the temperature and catalyst dependency of the uretdione selectivity, 0.5 ml of each reaction mixture was removed under nitrogen when $n_D^{20}$ values of 1.4550, 1.4670, 1.4740 and 1.4830 were reached, corresponding to resin yields of about 15, 35, 45 and 60% (cf. FIG. 1), and these samples were transferred to a NMR tube and, following the addition of 0.15 ml of a 1% solution of benzoyl chloride in $D_6$-DMSO (to deactivate the phosphine), were subjected to analysis by $^{13}$C-NMR spectroscopy.

For a better overeiw of the selectivities the parameter U/T was defined, as the molar ratio of the uretdione structures to the sum of the two trimer structures (isocyanurate and iminooxadiazinedione). The U/T values associated with the abovementioned yields (about 15, 35, 45 and 60% by weight respectively) are in Tables 2–5.

TABLE 2

U/T selectivities for about 15% by weight yield as a function of catalyst and reaction temperature

| Temperature [° C.] | U/T(TBP) | U/T(CHDHP) | U/T(DCPBP) | U/T(TCPP) |
|---|---|---|---|---|
| 40 | 4.0 | 4.2 | 7.4 | 10.2 |
| 60 | 4.9 | 5.3 | 7.5 | 32.9 |
| 80 | 6.8 | 7.2 | 13.4 | 37.3 |
| 100 | 7.2 | 12.3 | 11.4 | 41.7 |
| 120 | Experimental products unusable owing to excessive uretonimine fractions, cf. Table 6 | | | |

TABLE 3

U/T selectivities for about 35% by weight yield as a function of catalyst and reaction temperature

| Temperature [° C.] | U/T(TBP) | U/T(CHDHP) | U/T(DCPBP) | U/T(TCPP) |
|---|---|---|---|---|
| 40 | 3.2 | 3.6 | 5.7 | 8.0 |
| 60 | 3.4 | 4.3 | 5.8 | 11.3 |
| 80 | 3.4 | 4.1 | 4.8 | 8.1 |
| 100 | 3.2 | 2.7 | 2.8 | 4.1 |
| 120 | Experimental products unusable owing to excessive uretonimine fractions, cf. Table 7 | | | |

TABLE 4

U/T selectivities for about 45% by weight yield as a function of catalyst and reaction temperature

| Temperature [° C.] | U/T(TBP) | U/T(CHDHP) | U/T(DCPBP) | U/T(TCPP) |
|---|---|---|---|---|
| 40 | 2.8 | 3.3 | 4.8 | 6.9 |
| 60 | 2.7 | 3.8 | 4.9 | 8.2 |
| 80 | 2.4 | 3.1 | 3.5 | 5.1 |
| 100 | 2.5 | 1.7 | 1.9 | 2.1 |
| 120 | Experimental products unusable owing to excessive uretonimine fractions, cf. Table 8 | | | |

TABLE 5

U/T selectivities for about 60% by weight yield as a function of catalyst and reaction temperature

| Temperature [° C.] | U/T(TBP) | U/T(CHDHP) | U/T(DCPBP) | U/T(TCPP) |
|---|---|---|---|---|
| 40 | 2.2 | 2.8 | 3.5 | 5.3 |
| 60 | 1.6 | 3.0 | 3.6 | 5.7 |
| 80 | 1.3 | 2.1 | 2.5 | 3.1 |
| 100 | 1.9 | 1.0 | 1.2 | 1.0 |
| 120 | Experimental products unusable owing to excessive uretonimine fractions, cf. Table 9 | | | |

TABLE 6

Mol % of uretonimine formed in the reaction product for about 15% by weight yield as a function of catalyst and reaction temperature

| Temperature [° C.] | TBP | CHDHP | DCPBP | TCPP |
|---|---|---|---|---|
| 40 | n.n. | n.n. | n.n. | n.n. |
| 60 | n.n. | n.n. | n.n. | n.n. |
| 80 | n.n. | n.n. | n.n. | n.n. |
| 100 | n.n. | n.n. | n.n. | n.n. |
| 120 | 14.5 | 5.9 | 7.1 | n.n. |

TABLE 7

Mol % of uretonimine formed in the reaction product for about 35% by weight yield as a function of catalyst and reaction temperature

| Temperature [° C.] | TBP | CHDHP | DCPBP | TCPP |
|---|---|---|---|---|
| 40 | n.n. | n.n. | n.n. | n.n. |
| 60 | n.n. | n.n. | n.n. | n.n. |
| 80 | 1.1 | n.n. | n.n. | n.n. |
| 100 | 19.3 | 5.3 | n.n. | n.n. |
| 120 | 36.6 | 14.4 | 12.0 | n.n. |

TABLE 8

Mol % of uretonimine formed in the reaction product for about 45% by weight yield as a function of catalyst and reaction temperature

| Temperature [° C.] | TBP | CHDHP | DCPBP | TCPP |
|---|---|---|---|---|
| 40 | n.n. | n.n. | n.n. | n.n. |
| 60 | n.n. | n.n. | n.n. | n.n. |
| 80 | 4.2 | 1.6 | n.n. | n.n. |
| 100 | 32.8 | 6.6 | 6.0 | n.n. |
| 120 | 47.7 | 18.7 | 14.5 | 2.5 |

TABLE 9

Mol % of uretonimine formed in the reaction product for about 60% by weight yield as a function of catalyst and reaction temperature

| Temperature [° C.] | TBP | CHDHP | DCPBP | TCPP |
|---|---|---|---|---|
| 40 | n.n. | n.n. | n.n. | n.n. |
| 60 | n.n. | n.n. | n.n. | n.n. |
| 80 | 8.9 | 2.1 | 1.9 | n.n. |
| 100 | 53.1 | 8.5 | 7.3 | 1.5 |
| 120 | 64.3 | 25.0 | 18.2 | 3.2 |

Abbreviations

TBP: tri-n-butylphosphine (=> comparative experiments)

CHDHP: cyclohexyl-di-n-hexylphosphine (=> inventive experiment)

DCPBP: dicyclopentyl-butylphosphine (=> inventive experiment)

TCPP: tricyclopentylphosphine (=> inventive experiment)

n.n.: not detected by $^{13}$C-NMR spectroscopy

As can be inferred from the tables above, the uretdione selectivity of the catalysts of the invention is generally higher, for a given yield and with a low level of uretonimine in the products, than in the case of tri-n-butylphosphine (TBP). Also noteworthy at relatively high temperatures is the particularly low propensity towards formation of uretonimine when using the catalysts of the invention, this propensity always being significantly lower than when using TBP.

Examples 2

1500 g portions of HDI were freed from dissolved gasses under reduced pressure (0.5 mbar) with stirring at 60° C. for one hour in a stirred vessel, then blanketed with nitrogen, and, after they had cooled to 40° C., the following were added: 2-A: 6.0 g of TBP (=>comparative experiment) or 2-B: 21.0 g of DCPBP (=> inventive experiment).

Stirring was then continued at 40° C., and the increase in conversion was monitored by measuring the refraction. When an $n_D^{20}$ of about 1.4630 (target conversion) had been reached the products were worked up by distillation in a flash evaporator with upstream preevaporator at 0.3 mbar and with a heating medium temperature of 130° C. (preevaporator) and 140° C. (thin-film evaporator). The distillate was subsequently made up to the starting amount with fresh, degassed HDI under nitrogen, stirring was repeated at 40° C. until the abovementioned refractive index was reached, and then the product was worked up as described above. This sequence was repeated a total of 7 times. The reaction time required in each case is shown in Table 10, the data for the isolated resins in Table 11.

TABLE 10

Reaction times (hh:mm) of experiments 2-A and -B to target conversion

| Experiment | Catalyst | 1 | 2 | 3 | 4 | 5 | 6 | 7 | 8 |
|---|---|---|---|---|---|---|---|---|---|
| 2A | TBP | 04:01 | 05:08 | 03:10 | 04:25 | 03:38 | 09:40 | 12:27 | 14:24 |
| 2B | DCPBP | 14:09 | 12:48 | 13:13 | 12:31 | 13:03 | 12:00 | 15:18 | 16:37 |

TABLE 11

Data (average values of the 8 experiments) of the resins from the experiments
6-A: Comparative experiment, 6-B: inventive reaction

| Experiment | Catalyst | Yield [%] | NCO content [%] | Viscosity [mPas] | Colour number [APHA] | free HDI [%] | U/T |
|---|---|---|---|---|---|---|---|
| 2A | TBP | 27.9 | 22.3 | 130 | 53 | 0.12 | 2.8 |
| 2B | DCPBP | 30.0 | 22.2 | 82 | 35 | 0.07 | 4.1 |

When the inventive catalyst DCPBP was used the reaction regime observed was substantially more uniform than when using TBP. This is of critical significance for the practical usefulness of the phosphines in a process operated continuously. Moreover, in the process of the invention, resins with a lower viscosity, as a result of a higher uretdione fraction, were obtained in a higher yield. In addition, the resins prepared in accordance with the invention are distinguished by a lower HDI content.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of dimerizing isocyanates comprising reacting isocyanate functional compounds in the presence of phosphines containing at least one cycloaliphatic radical attached directly to phosphorus as catalysts resulting in the formation of uretdiones.

2. The method of claim 1, wherein the phosphines comprise phosphines described by formula I:

(I)

wherein
R$^1$ represents a C$_1$–C$_{12}$ alkyl- or alkoxy-substituted cycloaliphatic C$_3$–C$_{20}$ radical, and
R$^2$ and R$^3$ are each independently selected from C$_1$–C$_{12}$ alkyl- or alkoxy-substituted cycloaliphatic C$_3$–C$_{20}$ radical and a linear or branched aliphatic C$_1$–C$_{20}$ radical.

3. The method of claim 1, wherein the phosphines comprise a compound selected from the group consisting of cyclopentyldimethylphosphine, cyclopentyl-diethylphosphine, cyclopentyl-di-n-propylphosphine, cyclo-pentyl-di-isopropylphosphine, cyclopentyl-dibutylphosphine, cyclopentyl-dihexylphosphine, cyclopentyl-dioctylphosphine, dicyclopentyl-methyl-phosphine, dicyclopentyl-ethylphosphine, dicyclopentyl-n-propyl-phosphine, dicyclopentyl-isopropylphosphine, dicyclopentyl-butyl-phosphine, dicyclopentyl-hexylphosphine, dicyclopentyl-octylphosphine, tricyclopentylphosphine, cyclohexyl-dimethylphosphine, cyclohexyl-diethylphosphine, cyclohexyl-di-n-propylphosphine, cyclohexyl-di-isopropylphosphine, cyclohexyl-dibutylphosphine, cyclohexyl-dihexylphosphine, cyclohexyl-dioctylphosphine, dicyclohexyl-methylphosphine, dicyclohexyl-ethylphosphine, dicyclohexyl-n-propyl-phosphine, dicyclohexyl-isopropylphosphine, dicyclohexyl-butylphosphine, dicyclohexyl-hexylphosphine, dicyclohexyl-octylphosphine, and tricyclohexylphosphine.

4. A process for preparing polyisocyanates containing uretdione groups, comprising reacting
a) at least one organic isocyanate,
b) a catalyst comprising at least one phosphine containing at least one cycloaliphatic radical attached directly to phosphorus,
c) optionally one or more solvents, and
d) optionally one or more additives.

5. The process of claim 4, wherein the phosphines comprise phosphines described by formula I:

(I)

wherein
R$^1$ represents a C$_1$–C$_{12}$ alkyl- or alkoxy-substituted cycloaliphatic C$_3$–C$_{20}$ radical, and
R$^2$ and R$^3$ are each independently selected from C$_1$–C$_{12}$ alkyl- or alkoxy-substituted cycloaliphatic C$_3$–C$_{20}$ radical and a linear or branched aliphatic C$_1$–C$_{20}$ radical.

6. The process of claim 1, wherein the phosphines comprise a compound selected from the group consisting of cyclopentyldimethylphosphine, cyclopentyl-diethylphosphine, cyclopentyl-di-n-propylphosphine, cyclo-pentyl-di-isopropylphosphine, cyclopentyl-dibutylphosphine, cyclopentyl-dihexylphosphine, cyclopentyl-dioctylphosphine, dicyclopentyl-methylphosphine, dicyclopentyl-ethylphosphine, dicyclopentyl-n-propylphosphine, dicyclopentyl-isopropylphosphine, dicyclopentyl-butylphosphine, dicyclopentyl-hexylphosphine, dicyclopentyl-octylphosphine, tricyclopentylphosphine, cyclohexyl-dimethylphosphine, cyclohexyl-diethylphosphine, cyclohexyl-di-n-propylphosphine, cyclohexyl-di-isopropylphosphine, cyclohexyl-dibutylphosphine, cyclohexyl-dihexylphosphine, cyclohexyl-dioctylphosphine, dicyclohexyl-methylphosphine, dicyclohexyl-ethylphosphine, dicyclohexyl-n-propyl-phosphine, dicyclohexyl-isopropylphosphine, dicyclohexyl-butylphosphine, dicyclohexyl-hexylphosphine, dicyclohexyl-octylphosphine, and tricyclohexylphosphine.

7. The process of claim 4, wherein the amount of the catalyst is from 0.01 to 3 mol %, based on the molar amount of the isocyanate used.

8. The process of claim 4, wherein at least one organic isocyanate comprises an isocyanate selected from aliphatic isocyanates, cycloaliphatic isocyanates and araliphatic isocyanates, wherein the organic isocyanate has an NCO functionality of greater than 2.

9. The process of claim 8, wherein the isocyanate is one or more selected from the group consisting of hexamethylene diisocyanate, methylpentane diisocyanate, trimethylhexane diisocyanate, bis(isocyanatomethyl)-cyclohexane, norbornane diisocyanate, isophorone diisocyanate, bis(isocyanatocyclohexyl)methane, bis(isocyantomethyl)benzene and bis(2-isocyantoprop-2-yl)benzene (tetramethylxylylene diisocyanate.

10. The process of claim 4, wherein the one or more additives comprise one or more selected from the group consisting of antioxidants, light stabilizers, weak acids, and catalysts.

11. The process of claim 10, wherein the light stabilizer is a hindered amine light stabilizer.

12. The process of claim 10, wherein the catalyst comprises dibutyltin dilaurate.

13. The process of claim 4, wherein the solvent comprises one or more selected from the group consisting of aliphatic hydrocarbons, aromatic hydrocarbons, alcohols, ketones, esters, and ethers.

* * * * *